(12) United States Patent
Sandell et al.

(10) Patent No.: US 9,180,137 B2
(45) Date of Patent: Nov. 10, 2015

(54) PREPARATION OF BONE CEMENT COMPOSITIONS

(75) Inventors: Veronica Sandell, Bjärred (SE); Malin Nilsson, Hudiksvall (SE); Eva Liden, Lund (SE); Jeffrey C. Karr, Lakeland, FL (US)

(73) Assignee: BONE SUPPORT AB (SE)

( * ) Notice: Subject to any disclaimer, the term of this patent is extended or adjusted under 35 U.S.C. 154(b) by 155 days.

(21) Appl. No.: 13/022,771

(22) Filed: Feb. 8, 2011

(65) Prior Publication Data

US 2012/0129761 A1    May 24, 2012

Related U.S. Application Data

(60) Provisional application No. 61/302,596, filed on Feb. 9, 2010.

(51) Int. Cl.
*A61K 31/7052* (2006.01)
*A61K 31/546* (2006.01)
(Continued)

(52) U.S. Cl.
CPC ............ *A61K 31/7052* (2013.01); *A61K 31/545* (2013.01); *A61K 31/546* (2013.01);
(Continued)

(58) Field of Classification Search
CPC ............ A61K 31/7052; A61K 31/546; A61K 31/7036; A61K 31/702; A61K 31/545; A61L 27/12; A61L 24/02; A61L 27/025; A61L 24/0015; A61L 27/54; A61L 2300/406
See application file for complete search history.

(56) References Cited

U.S. PATENT DOCUMENTS

| 949,163 A | 2/1910 | Stapley |
|---|---|---|
| 1,644,173 A | 10/1927 | Carr |

(Continued)

FOREIGN PATENT DOCUMENTS

| DE | 44 09 610 A1 | 9/1995 |
|---|---|---|
| DE | 202 16 632 U1 | 3/2004 |

(Continued)

OTHER PUBLICATIONS

Lei et al, Mechanical Properties of Calcium Sulphate/hydroxyapatite Cement, 2006, Bio-Medical Materials and Engineering, 16, 423-428.*

(Continued)

*Primary Examiner* — Trevor Love
(74) *Attorney, Agent, or Firm* — Finnegan, Henderson, Farabow, Garrett & Dunner, LLP

(57) ABSTRACT

A method for the preparation of injectable ready-to-use paste bone cement compositions by mixing a dry inorganic bone cement powder comprising a particulate calcium sulfate hemihydrate capable of hardening in vivo by hydration of the calcium sulfate hemihydrate forming calcium sulfate dihydrate, an aqueous liquid and an additive that normally retards the setting process, said method comprising
a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component
b) mixing the bone cement powder with the aqueous liquid for a period of time
c) leaving the mixture for the time needed for allowing the hydration reaction of the calcium sulfate hemihydrate to proceed and allowing calcium sulfate dihydrate crystals to form and grow, and d) admixing the additive by means of a short-duration mixing using a minimum of energy
surprisingly shortens the setting times for the cement comprising the additive that retard the setting process to the level observed in the absence of the additive and enables a complete hydration of calcium sulfate hemihydrate to calcium sulfate dihydrate, even when using additives else preventing the hardening.

16 Claims, 6 Drawing Sheets

(51) Int. Cl.
  *A61L 27/12* (2006.01)
  *A61L 24/02* (2006.01)
  *A61L 27/02* (2006.01)
  *A61K 31/7036* (2006.01)
  *A61L 24/00* (2006.01)
  *A61K 31/702* (2006.01)
  *A61L 27/54* (2006.01)
  *A61K 31/545* (2006.01)

(52) U.S. Cl.
  CPC .......... *A61K31/702* (2013.01); *A61K 31/7036* (2013.01); *A61L 24/0015* (2013.01); *A61L 24/02* (2013.01); *A61L 27/025* (2013.01); *A61L 27/12* (2013.01); *A61L 27/54* (2013.01); *A61L 2300/406* (2013.01); *A61L 2400/06* (2013.01)

(56) References Cited

U.S. PATENT DOCUMENTS

| | | |
|---|---|---|
| 1,865,912 A | 7/1932 | Horn |
| 2,545,017 A | 3/1951 | Billingsley |
| 3,367,783 A | 2/1968 | Billerbeck |
| 3,475,010 A | 10/1969 | Cook et al. |
| 3,570,719 A | 3/1971 | Schiff |
| 3,688,765 A | 9/1972 | Gasaway |
| 3,837,379 A | 9/1974 | McDonald et al. |
| 3,965,910 A | 6/1976 | Fischer |
| 4,001,323 A | 1/1977 | Felder et al. |
| 4,139,605 A | 2/1979 | Felder et al. |
| 4,240,425 A | 12/1980 | Akhavi |
| 4,269,331 A | 5/1981 | Watson |
| 4,338,925 A | 7/1982 | Miller |
| 4,348,377 A | 9/1982 | Felder et al. |
| 4,487,766 A | 12/1984 | Mach |
| 4,496,342 A | 1/1985 | Banko |
| 4,518,430 A | 5/1985 | Brown et al. |
| 4,583,974 A | 4/1986 | Kokernak |
| 4,612,053 A | 9/1986 | Brown et al. |
| 4,619,655 A | 10/1986 | Hanker et al. |
| 4,673,296 A | 6/1987 | Sjogren |
| 4,676,655 A | 6/1987 | Handler |
| 4,721,390 A | 1/1988 | Lidgren |
| 4,752,479 A | 6/1988 | Briggs et al. |
| 4,832,500 A | 5/1989 | Brunold et al. |
| 4,994,442 A | 2/1991 | Gil et al. |
| 5,047,030 A | 9/1991 | Draenert |
| 5,071,040 A | 12/1991 | Laptewicz, Jr. |
| 5,073,362 A | 12/1991 | Blaszkiewicz et al. |
| 5,149,368 A | 9/1992 | Liu et al. |
| 5,168,757 A | 12/1992 | Rabenau et al. |
| 5,232,024 A | 8/1993 | Williams |
| 5,252,301 A | 10/1993 | Nilson et al. |
| 5,262,166 A | 11/1993 | Liu et al. |
| 5,269,785 A | 12/1993 | Bonutti |
| 5,281,265 A | 1/1994 | Liu |
| 5,328,262 A | 7/1994 | Lidgren et al. |
| 5,328,462 A | 7/1994 | Fischer |
| 5,342,441 A | 8/1994 | Mandal et al. |
| 5,360,823 A | 11/1994 | Griffel et al. |
| 5,403,318 A | 4/1995 | Boehringer et al. |
| 5,447,711 A | 9/1995 | Almen et al. |
| 5,462,722 A | 10/1995 | Liu et al. |
| 5,501,520 A | 3/1996 | Lidgren et al. |
| 5,549,380 A | 8/1996 | Lidgren et al. |
| 5,551,778 A | 9/1996 | Hauke et al. |
| 5,605,885 A | 2/1997 | Bernton et al. |
| 5,614,206 A | 3/1997 | Randolph et al. |
| 5,650,108 A | 7/1997 | Nies et al. |
| 5,665,066 A | 9/1997 | Fischer |
| 5,681,873 A | 10/1997 | Norton et al. |
| 5,695,742 A | 12/1997 | Felder et al. |
| 5,698,186 A | 12/1997 | Weeks |
| 5,756,127 A | 5/1998 | Grisoni et al. |
| 5,766,247 A | 6/1998 | Aoki et al. |
| 5,797,873 A | 8/1998 | Franz et al. |
| 5,829,875 A | 11/1998 | Hagel et al. |
| 5,837,752 A | 11/1998 | Shastri et al. |
| 5,842,786 A | 12/1998 | Solomon |
| 5,866,100 A | 2/1999 | Tournier et al. |
| 5,871,549 A | 2/1999 | Jayashankar et al. |
| 5,891,423 A | 4/1999 | Weeks |
| 5,965,772 A | 10/1999 | Desantis |
| 5,997,544 A | 12/1999 | Nies et al. |
| 6,018,094 A | 1/2000 | Fox |
| 6,018,095 A | 1/2000 | Lerch et al. |
| 6,027,742 A | 2/2000 | Lee et al. |
| 6,062,722 A | 5/2000 | Lake |
| 6,071,982 A | 6/2000 | Wise et al. |
| 6,074,358 A | 6/2000 | Andrew et al. |
| 6,075,067 A | 6/2000 | Lidgren |
| 6,080,801 A | 6/2000 | Draenert et al. |
| 6,118,043 A | 9/2000 | Nies et al. |
| 6,120,174 A | 9/2000 | Hoag et al. |
| 6,206,957 B1 | 3/2001 | Driessens et al. |
| 6,231,615 B1 | 5/2001 | Preissman |
| 6,248,110 B1 | 6/2001 | Reiley et al. |
| 6,251,139 B1 | 6/2001 | Lin et al. |
| 6,309,420 B1 | 10/2001 | Preissman |
| 6,365,218 B1 | 4/2002 | Borschel et al. |
| 6,367,962 B1 | 4/2002 | Mizutani et al. |
| 6,431,743 B1 | 8/2002 | Mizutani et al. |
| 6,440,138 B1 | 8/2002 | Reiley et al. |
| 6,447,809 B1 | 9/2002 | Krumhar et al. |
| 6,485,428 B1 | 11/2002 | Enk |
| 6,488,651 B1 | 12/2002 | Morris et al. |
| 6,586,009 B1 | 7/2003 | Lidgren |
| 6,596,904 B1 | 7/2003 | Dunn et al. |
| 6,689,375 B1 | 2/2004 | Wahlig et al. |
| 6,706,069 B2 | 3/2004 | Berger |
| 6,706,273 B1 | 3/2004 | Roessler |
| 6,716,216 B1 | 4/2004 | Boucher et al. |
| 6,719,761 B1 | 4/2004 | Reiley et al. |
| 6,723,334 B1 | 4/2004 | McGee et al. |
| 6,736,537 B2 | 5/2004 | Coffeen et al. |
| 6,740,090 B1 | 5/2004 | Cragg et al. |
| 6,897,339 B2 | 5/2005 | Turchetta et al. |
| 7,160,306 B2 | 1/2007 | Matsuzaki et al. |
| 7,393,342 B2 | 7/2008 | Henniges et al. |
| 7,393,405 B2 | 7/2008 | Bohner |
| 7,407,542 B2 | 8/2008 | Lemaitre et al. |
| 7,417,077 B2 | 8/2008 | Lidgren et al. |
| 7,524,103 B2 | 4/2009 | McGill et al. |
| 7,771,705 B2 | 8/2010 | Zhao |
| 7,972,630 B2 | 7/2011 | Lidgren |
| 8,420,127 B2 | 4/2013 | Lidgren et al. |
| 8,574,550 B2 | 11/2013 | Zhao |
| 2001/0012968 A1 | 8/2001 | Preissman |
| 2001/0051670 A1 | 12/2001 | Goupil et al. |
| 2002/0055143 A1 | 5/2002 | Bell et al. |
| 2002/0076378 A1 | 6/2002 | Wolfe et al. |
| 2002/0101785 A1 | 8/2002 | Edwards et al. |
| 2002/0156483 A1 | 10/2002 | Voellmicke et al. |
| 2002/0169506 A1 | 11/2002 | Matsushima et al. |
| 2003/0018339 A1 | 1/2003 | Higueras et al. |
| 2003/0028251 A1 | 2/2003 | Matthews |
| 2003/0040718 A1 | 2/2003 | Kust et al. |
| 2003/0049329 A1 | 3/2003 | Lee et al. |
| 2003/0050702 A1 | 3/2003 | Berger |
| 2003/0055512 A1 | 3/2003 | Genin et al. |
| 2003/0109883 A1 | 6/2003 | Matsuzaki et al. |
| 2003/0161858 A1 | 8/2003 | Lidgren |
| 2003/0181986 A1 | 9/2003 | Buchholz |
| 2004/0006347 A1 | 1/2004 | Sproul |
| 2004/0048947 A1 | 3/2004 | Lidgren et al. |
| 2004/0049202 A1 | 3/2004 | Berger |
| 2004/0068234 A1 | 4/2004 | Martin et al. |
| 2004/0068266 A1 | 4/2004 | Delmotte |
| 2004/0137032 A1 | 7/2004 | Wang |
| 2004/0151751 A1 | 8/2004 | Cooper |
| 2004/0191897 A1 | 9/2004 | Muschler |
| 2004/0244651 A1 | 12/2004 | Lemaitre et al. |
| 2005/0015074 A1 | 1/2005 | Trombley, III |
| 2005/0023171 A1 | 2/2005 | Delaney et al. |

(56) References Cited

U.S. PATENT DOCUMENTS

| | | |
|---|---|---|
| 2005/0105385 A1 | 5/2005 | McGill et al. |
| 2005/0119746 A1 | 6/2005 | Lidgren |
| 2005/0128868 A1 | 6/2005 | Vries |
| 2005/0197629 A1 | 9/2005 | Conway |
| 2005/0241535 A1 | 11/2005 | Bohner |
| 2005/0251149 A1 | 11/2005 | Wenz |
| 2005/0257714 A1 | 11/2005 | Constantz et al. |
| 2005/0287071 A1 | 12/2005 | Wenz |
| 2006/0004358 A1 | 1/2006 | Serhan et al. |
| 2006/0036211 A1 | 2/2006 | Solsberg et al. |
| 2006/0041033 A1 | 2/2006 | Bisig et al. |
| 2006/0122621 A1 | 6/2006 | Truckai et al. |
| 2007/0041906 A1 | 2/2007 | Lidgren et al. |
| 2007/0161943 A1 | 7/2007 | Lidgren et al. |
| 2007/0217282 A1 | 9/2007 | Lidgren et al. |
| 2008/0065088 A1 | 3/2008 | Hughes et al. |
| 2008/0096797 A1 | 4/2008 | Li et al. |
| 2008/0161752 A1 | 7/2008 | Rajala et al. |
| 2008/0318862 A1 | 12/2008 | Ashman et al. |
| 2010/0249753 A1 | 9/2010 | Gaisser et al. |

FOREIGN PATENT DOCUMENTS

| | | | |
|---|---|---|---|
| EP | 0 023 992 A1 | 2/1981 | |
| EP | 0 109 310 B1 | 5/1984 | |
| EP | 0 308 364 A2 | 3/1989 | |
| EP | 0 495 284 A1 | 7/1992 | |
| EP | 0 639 382 A1 | 2/1995 | |
| EP | 0 639 382 B1 | 2/1995 | |
| EP | 0 657 208 A1 | 6/1995 | |
| EP | 0 520 690 B1 | 11/1995 | |
| EP | 0 807 432 B1 | 11/1997 | |
| EP | 0 835 668 B1 | 4/1998 | |
| EP | 0 950 420 A2 | 10/1999 | |
| EP | 1 002 513 | 5/2000 | |
| EP | 1 155 704 A2 | 11/2001 | |
| EP | 1 296 909 B1 | 1/2002 | |
| EP | 1 208 850 A1 | 5/2002 | |
| EP | 1 132 061 B1 | 8/2004 | |
| EP | 1 610 832 B1 | 1/2006 | |
| EP | 1 712 244 A1 | 10/2006 | |
| EP | 1 891 984 A1 | 2/2008 | |
| EP | 2 660 267 A1 | 11/2013 | |
| ES | 2 178 556 | 12/2002 | |
| GB | 2 239 818 A | 7/1991 | |
| GB | 2 338 428 A | 12/1999 | |
| JP | 64-22256 A | 1/1989 | |
| JP | 64-22257 A | 1/1989 | |
| JP | 1-139516 | 6/1989 | |
| JP | 5-168692 A | 7/1993 | |
| JP | 5-507862 A | 11/1993 | |
| JP | 9-502368 | 3/1997 | |
| JP | 2935708 B2 | 8/1999 | |
| JP | 2000-000295 A | 1/2000 | |
| JP | 2000-159564 | 6/2000 | |
| JP | 2001-106638 A | 4/2001 | |
| JP | 2001-510078 A | 7/2001 | |
| JP | 2001-517997 A | 10/2001 | |
| JP | 2001-517997 T | 10/2001 | |
| JP | 2002-058736 A | 2/2002 | |
| JP | 2002-325831 A | 11/2002 | |
| JP | 2003-507090 A | 2/2003 | |
| JP | 2004-503332 | 2/2004 | |
| JP | 2004-503332 A | 2/2004 | |
| SE | 8903538 | 4/1991 | |
| WO | WO 85/01727 A1 | 4/1985 | |
| WO | WO 87/05521 A1 | 9/1987 | |
| WO | WO 88/06023 | 8/1988 | |
| WO | WO 89/03695 A1 | 5/1989 | |
| WO | WO 91/00252 A1 | 1/1991 | |
| WO | WO 91/17722 A1 | 11/1991 | |
| WO | WO 93/14799 A1 | 8/1993 | |
| WO | WO 95/07108 | 3/1995 | |
| WO | WO 96/14265 | 5/1996 | |
| WO | WO 96/39202 A1 | 12/1996 | |
| WO | WO 97/38676 A1 | 10/1997 | |
| WO | WO 97/47334 A1 | 12/1997 | |
| WO | WO 99/17710 | 4/1999 | |
| WO | WO 99/62570 A1 | 12/1999 | |
| WO | WO 99/65597 A1 | 12/1999 | |
| WO | WO 00/02597 A1 | 1/2000 | |
| WO | WO 00/26179 | 5/2000 | |
| WO | WO 00/45867 A1 | 8/2000 | |
| WO | WO 01/34216 | 5/2001 | |
| WO | WO 01/34216 A1 | 5/2001 | |
| WO | WO 01/76649 | 10/2001 | |
| WO | WO 01/76649 A1 | 10/2001 | |
| WO | WO 02/05861 | 1/2002 | |
| WO | WO 02/05861 A1 | 1/2002 | |
| WO | WO 02/058755 A2 | 8/2002 | |
| WO | WO 02/080933 A1 | 10/2002 | |
| WO | WO 03/011957 | 2/2003 | |
| WO | WO 03/037165 A2 | 5/2003 | |
| WO | WO 03/041753 | 5/2003 | |
| WO | WO 03/053488 | * 7/2003 | ............ A61L 27/02 |
| WO | WO 03/053488 A1 | 7/2003 | |
| WO | WO 2004/000374 | 12/2003 | |
| WO | WO 2004/002615 A1 | 1/2004 | |
| WO | WO 2004/026377 A1 | 4/2004 | |
| WO | WO 2004/050131 | 6/2004 | |
| WO | WO 2004/078223 A1 | 9/2004 | |
| WO | WO 2004/087229 | 10/2004 | |
| WO | WO 2004/091435 | 10/2004 | |
| WO | WO 2005/099783 A1 | 10/2005 | |
| WO | WO 2005/122971 A1 | 12/2005 | |
| WO | WO 2006/015316 | 2/2006 | |
| WO | WO 2006/041365 A1 | 4/2006 | |
| WO | WO 2006/118461 | 11/2006 | |
| WO | WO 2007/143698 | 12/2007 | |
| WO | WO 2008/023254 | 2/2008 | |
| WO | WO 2009/081169 | 7/2009 | |
| WO | WO 2011/098438 | 8/2011 | |

OTHER PUBLICATIONS

Gitelis, S. and Breback, G. T., "The treatment of chronic osteomyelitis with a biodegradable antibiotic-impregnated implant," *J. Orthopaedic Surgery* (2002) 10(1):52-60.

Karr, J. C., "Management of a Diabetic Patient Presenting with Forefoot Osteomyelitis: The use of Cerament™|BoneVoid Filler Impregnated with Cancomycin—An Off Label Use," *J. Diabetic Foot Complications* (2009) 1(4):94-100.

Richelsoph, K. C. et al., "Elution Behavior of Daptomycin-loaded Calcium Sulfate Pellets," *Clin. Orthopaedics and Related Res.* (2007) 461:68-73.

Singh, N. B. and Middendorf, B., "Calcium sulphate hemihydrate hydration leading to gypsum crystallization," *Prog. Crystal Growth & Characterization of Materials* (2007) 53:57-77.

"Powder (substance)" entry from www.wikipedia.com, http://en.wikipedia.org/wiki/Powder_(substance)>> (last visited Dec. 1, 2008).

Aebli et al., "Cardiovascular Changes During Multiple Vertebroplasty With and Without Vent-Hole," *Spine* (2003)28(14):1504-1512.

U.S. Appl. No. 13/613,563, filed Sep. 13, 2012.

U.S. Appl. No. 10/257,561; (U.S. Pat Pub. No. 2003/0161858), filed Oct. 11, 2002.

U.S. Appl. No. 10/333,026, filed Jan. 15, 2003 and issued Aug. 26, 2008 as U.S. Patent No. 7,417,077.

U.S. Appl. No. 10/499,023; (U.S. Pat. Pub. No. 2005/0119746), filed Jun. 18, 2004.

U.S. Appl. No. 10/578,734, (U.S. Pat. Pub. No. 2007/0161943), filed May 10, 2006.

U.S. Appl. No. 11/587,313 (U.S. Pat. Pub. No. 2007/0217282), filed Oct. 23, 2006.

U.S. Appl. No. 12/122,873 (U.S. Pat. Pub. No. 2008/0286331), filed May 19, 2008.

U.S. Appl. No. 12/219,642 (U.S. Pat. Pub. No. 2009/0018667), filed Jul. 23, 2008.

(56) References Cited

OTHER PUBLICATIONS

U.S. Appl. No. 12/219,543 (U.S. Pat. Pub. No. 2009/0192629), filed Jul. 23, 2008.
U.S. Appl. No. 12/911,198, filed Oct. 25, 2010.
U.S. Appl. No. 12/911,266, filed Oct. 25, 2010.
Barbalace, K. "Chemical Database: Calcium sulfate", Environmental Chemistry.com (2009).
Bohner et al., "Effects of Sulfate Ions on the in Vitro Properties of β-TCP-MCPM-Water Mixtures. Preliminary in Vivo Results," *Bioceramics: Materials and Applications, Ceramic Transactions* (1995), 48:245-259.
Bohner, "New hydraulic cements based on a-tricalcium phosphate-calcium sulfate dihydrate mixtures," *Biomaterials* (2004) 25: 741-749.
Bohner, M., "Physical and chemical aspects of calcium phosphates used in spinal surgery", *Eur. Spine J.* (2001) 10:S114-S121.
Cabañas, "Setting Behavior and in Vitro Bioactivity of Hydroxyapatite/Calcium Sulfate Cements," *Chem. Mater.* (2002) 14; 3550-3555.
Cahn, R.W., ed. "Materials Science and Technology: A Comprehensive Treatment," *Weinheim*,(1992) 14:70-109.
Damien, C.J. Student Research Award in the Graduate Degree Candidate Category, 16th Annual Meeting of the Society for Biomaterials, Charleston, SC, May 20-23, 1990; *Journal of Biomedical Materials Research*(1990), 24:639-654.
Database Derwent WPI: Week 198928, Derwent Publications Ltd., JP 1-139516.
Database Derwent WPI: Week 199126, Derwent Publications Ltd., SE 8903538.
Database Derwent WPI: Week 199433, Derwent Publications Ltd., London, GB: Class A 96, AN 1994-269325 & JP 61-99623 A (Lion Corp. et al.), Jul. 19, 1994.
Database Derwent WPI: Week 199734, Derwent Publications Ltd., EP 0 807 432 B1.
Database Derwent WPI: Week 200138, Derwent Publications Ltd., WO 2001/34216 A1.
De Robertis et al., "Solubility of some calcium-caboxylic ligand complexes in aqueous solution," *Talanta* (1995) 42:1651-1662.
Elliott, J. C. "General Chemistry of the Calcium Orthophosphates," in Structure and Chemistry of the Apatites and Other Calcium Orthophosphates, 1994, Elsevier: Netherlands, Chapter 1, pp. 1-9.
English language abstract of EP 1 002 513 from Espacenet.
English language abstract of JP 2000-159564 from Espacenet.
English Language abstract of JP 2000-000295 A.
English language abstract of JP 2001-106638 A.
English language abstract of JP 2001-517997 T.
English language abstract of JP 2002-325831 A.
English language abstract of JP 2935708 B2.
English language abstract of JP 5-168692 A.
English language translation of JP 64-22256.
English-Language Abstract of EP 0 657 208 A1.
English-Language translation of JP 1-139516.
English language translation of Japanese Office Action dated Jun. 2, 2009 in Japanese Application No. 2003-554244 related to U.S. Appl. No. 10/499,023.
English language translation of Japanese Office Action mailed on Jun. 1, 2010 in Japanese Application No. 2006-539432 related to U.S. Appl. No. 10/578,734.
English language translation of Japanese Office Action dated Sep. 9, 2010 in Japanese Application No. 2006-507949 related to U.S. Appl. No. 10/547,671.
English language translation of Office Action for Japanese Patent Application 2001-574164, corresponding to U.S. Appl. No. 10/257,561 dated Feb. 2, 2011.
English language translation of Japanese Office Action, dated Oct. 3, 2011, for Japanese Patent Application No. 2002-511972.
English-language translation of ES 2 178 556 A1, "Calcium sulfate cement capable of controlled biodegradation".
Engqvist et al., "Chemical Stability of a Novel Injectable Bioceramic for Stabilisation of Vertebral Compression Fractures," *Trends Biomater. Artif. Organs* (2008) 21(2):98-106.
Eromosele et al., "Characterization and viscosity parameters of seed oils from wild plants", *Science Direct: Bioresource Technology* (2002).
Ima-Nirwana et al., "Palm vitamin E improves bone metabolism and survival rate in thyrotoxic rats," *Gen. Pharmacol.* (1999) 32;621-626.
International Preliminary Examination Report for PCT/SE01/00789 dated Jan. 11, 2002 related to U.S. Appl. No. 10/257,561.
International Preliminary Examination Report for PCT/SE01/01627 dated Oct. 14, 2002, related to U.S. Appl. No. 10/333,026.
International Preliminary Examination Report for PCT/SE02/02428 dated Mar. 16. 2004, related to U.S. Appl. No. 10/499,023.
International Preliminary Examination Report for PCT/SE2004/000328 dated Aug. 30, 2005, related to U.S. Appl. No. 10/547,671.
nternational Preliminary Report on Patentability for PCT/SE2004/001626 dated Feb. 13, 2006.
International Preliminary Report on Patentability for PCT/SE2005/000932 dated Dec. 28, 2006.
International Search Report for PCT/SE01/00789 dated Jul. 9, 2001, related to U.S. Appl. No. 10/257,561.
International Search Report for PCT/SE01/01627 dated Dec. 18, 2001, related to U.S. Appl. No. 10/333,026.
International Search Report for PCT/SE02/02428 dated Apr. 4, 2003, related to U.S. Appl. No. 10/499,023.
International Search Report for PCT/SE2004/000328 dated Jun. 8, 2004, related to U.S. Appl. No. 10/547,671.
International Search Report for PCT/SE2004/001626 dated Feb. 28, 2005.
International Search Report for PCT/SE2005/000932 dated Oct. 10, 2005.
Kirby et al., "Acute Bronchospasm Due to Exposure to Polymethylmethacrylate Vapors during Percutaneous Vertebroplasty," *AJR* (2003) 180:543-544.
Koessler et al., "Fat and Bone Marrow Embolism During Percutaneous Vertebroplasty," *Anesth. Analg.* (2003) 97:293-294.
Komath et al., "On the development of an apatic calcium phosphate bone cement," *Bull. Mater. Sci* (2000) 23(2):135-140.
Lei, D. et al. "Mechanical Properties of Calcium Sulphate/hydroxyapatite Cement," *Bio-Medical Materials and Engineering* (2006) 16:423-428.
Lidgren, "Bone Substitutes," *Karger Gazette* (2002) 65:1-4.
Machine Translation of JP-A-2002-058736.
Mirtchi et al., "Calcium phosphate cements: action of setting regulators on the properties of the β-tricalcium phosphate-monocalcium phosphate cements," *Biomaterials* (1989), 10(9): 634-638.
Nilsson et al., "Biodegradation and biocompatability of a calcium sulphate-hydroxyapatite bone substitute," *J. of Bone & Joint Surgery (Br)* (2004) 86-8:120-125.
Nilsson et al., "Characterization of a novel calcium phosphate/sulphate bone cement," *J. Biomedical Materials Research* (2002) 61(4): 600-607.
Nilsson et al., "New Perspectives of Bioactivesdaicium Phosphate Cements for Biomedical Applications," Research Centre in Biomedical Engineering, Dept. of Material Science and Metallurgy, Universitat Politecnica de Catalunya, Avda, Diagonal 647k Barcelona, E-08028, Spain, pp. 95-99, Nov. 2000.
Nilsson et al., "The Effect of Aging an Injectable Bone Graft Substitute in Simulated Body Fluid," *Key Engineering Materials* (2003) 240-242: 403-406.
Notice of Allowance in U.S. Appl. No. 10/333,026 dated Apr. 25, 2008.
Notice of Allowance in U.S. Appl. No. 10/578,734 dated Jul. 27, 2010 (Examiner Merene).
Notice of Allowance in U.S. Appl. No. 10/578,734 dated Dec. 29, 2010 (Examiner Merene).
Notice of Allowance in U.S. Appl. No. 11/587,313 dated Jan. 26, 2011 (Examiner Soohoo).
Notice of Allowance in U.S. Appl. No. 10/257,561 dated Feb. 23, 2011 (Examiner Meller).
Notice of Allowance in U.S. Appl. No. 12/585,194 dated Mar. 22, 2012 (Examiner Soohoo).

(56) References Cited

OTHER PUBLICATIONS

Notice of Allowance in U.S. Appl. No. 12/585,194 dated Jun. 22, 2012.
Notice of Allowance in U.S. Appl. No. 10/547,671 dated Dec. 26, 2012 (Examiner Deberry).
Office Action in U.S. Appl. No. 10/257,561 dated Sep. 5, 2006.
Office Action in U.S. Appl. No. 10/257,561 dated Mar. 28, 2007.
Office Action in U.S. Appl. No. 10/257,561 date Oct. 15, 2007.
Office Action in U.S. Appl. No. 10/257,561 dated Jul. 2, 2008.
Office Action in U.S. Appl. No. 10/257,561 dated Apr. 3, 2009 (Examiner Meller).
Office Action in U.S. Appl. No. 10/257,561 dated Nov. 10, 2009 (Examiner M. Meller).
Office Action in U.S. Appl. No. 10/257,561 dated Apr. 27, 2010 (Examiner Meller).
Office Action in U.S. Appl. No. 10/333,026 dated Mar. 21, 2006.
Office Action in U.S. Appl. No. 10/333,026 dated Oct. 31, 2006.
Office Action in U.S. Appl. No. 10/333,026 dated Oct. 10, 2007.
Office Action in U.S. Appl. No. 10/499,023 dated Oct. 4, 2007.
Office Action in U.S. Appl. No. 10/499,023 dated Jul. 22, 2008.
Office Action in U.S. Appl. No. 10/499,023 dated Apr. 17, 2009 (Examiner Orwig).
Office Action in U.S. Appl. No. 10/499,023 dated Sep. 9, 2009 (Examiner Orwig).
Office Action in U.S. Appl. No. 10/499,023 dated Jun. 10, 2010 (Examiner Orwig).
Office Action in U.S. Appl. No. 10/499,023 dated Jan. 11, 2013 (Examiner Orwig).
Office Action in U.S. Appl. No. 10/547,671 dated Aug. 5. 2009.
Office Action in U.S. Appl. No. 10/547,671 dated May 5, 2010 (Examiner Deberry).
Office Action in U.S. Appl. No. 10/547,671 dated Aug. 16, 2010 (Examiner Deberry).
Office Action in U.S. Appl. No. 10/547,671 dated Aug. 23, 2011 (Examiner Deberry).
Office Action in U.S. Appl. No. 10/547,671 dated May 29, 2012 (Examiner Deberry).
Office Action in U.S. Appl. No. 10/578,734 dated Oct. 26, 2009 (Examiner Merene).
Office Action in U.S. Appl. No. 11/587,313 dated Jun. 18, 2010 (Examiner Soohoo).
Office Action in U.S. Appl. No. 12/122,873 dated Jun. 19, 2009 (Examiner Yoon).
Office Action in U.S. Appl. No. 12/122,873 dated Oct. 29, 2009 (Examiner Yoon).
Office Action in U.S. Appl. No. 12/122,873 dated Mar. 19, 2010 (Examiner Yoon).
Office Action in U.S. Appl. No. 12/122,873 dated Sep. 8, 2010 (Examiner Yoon).
Office Action in U.S. Appl. No. 12/122,873 dated Feb. 27, 2012 (Examiner Yoon).
Office Action in U.S. Appl. No. 12/219,542 dated Jun. 19, 2009 (Examiner Yoon).
Office Action in U.S. Appl. No. 12/219,542 dated Jan. 11, 2010 (Examiner Yoon).
Office Action in U.S. Appl. No. 12/219,542 dated Jun. 25, 2010 (Examiner Yoon).
Office Action in U.S. Appl. No. 12/219,542 dated Mar. 1, 2012 (Examiner Yoon).
Office Action in U.S. Appl. No. 12/219,543 dated Mar. 19, 2010 (Examiner Yoon).
Office Action in U.S. Appl. No. 12/219,543 dated Sep. 8, 2010 (Examiner Yoon).
Office Action in U.S. Appl. No. 12/219,543 dated Feb. 27, 2012 (Examiner Yoon).
Office Action in U.S. Appl. No. 12/585,194 dated Aug. 11, 2011 (Examiner SooHoo).
Parsons, John R., et al., "Osteoconductive Composite Grouts for Orthopedic Use", pp. 190-207.
Starling, S., "EFSA Says Calcium Sulphate Safe in Supplements" (2008), Nutraingredients.com.
Supplemental Notice of Allowance in U.S. Appl. No. 10/578,734 dated Sep. 17. 2010 (Examiner Merene).
Technical Specification, Calcium Sulfate Hemihydrate Food Grade, 2009.
Written Opinion of the International Searching Authority for PCT/SE2004/001626 dated Feb. 28, 2005.
Written Opinion of the International Searching Authority for PCT/SE2005/000932 dated Oct. 10, 2005.
U.S. Appl. No. 10/547,671 (U.S. Pat. Pub. No. 2007/0041906), filed Sep. 2, 2005.
U.S. Appl. No. 12/585,194 (U.S. Pat. Pub. No. 2010/0008181), filed Sep. 8, 2009.
English language translation of Japanese Office Action dated May 26, 2010 in Japanese Application No. 2006-539432 related to U.S. Appl. No. 10/578,734; (12 pages).
Examiner Interview Summary in U.S. Appl. No. 13/022,771 dated Apr. 3, 2013 (Examiner Love), 3 pages.
Liu, Da, et al.; "Augmentation of Pedicle Screw Stability With Calcium Sulfate Cement in Osteoporotic Sheer;" J Spinal Disord Tech, vol. 24, No. 4; Jun. 2011, pp. 235-241.
Notice of Allowance in U.S. Appl. No. 10/499,023 dated Jul. 17, 2013.
Notice of Allowance in U.S. Appl. No. 13/613,563 dated Oct. 16, 2013.
Office Action (Final Rejection) in U.S. Appl. No. 13/022,771 dated Aug. 8, 2013.
Office Action in U.S. Appl. No. 13/022,771 dated Nov. 14, 2012 (Examiner Love), 9 pages.
Office Action in U.S. Appl. No. 3/613,563, dated May 14, 2013 (Examiner SooHoo).
Office Action in U.S. Appl. No. 13/799,959 dated Jul. 16, 2013 (Examiner Deberry).
Yi, Xiaodong, et al.; "Augmentation of Pedicle Screw Fixation Strength Using an Injectable Calcium Sulfate Cement;" *Spine*, vol. 33, No. 23; pp. 2503-2509; 2008.
Zampelis, Vasilis, et al., "The Effect of a Biphasic Injectable Bone Substitute on the Interface Strength in a Rabbit Knee Prosthesis Model;" Journal of Orthopaedic Surgery and Research; 2013.
Acarturk et al., "Bone Healing Response to an Injectable Calcium Phosphate Cement With Enhanced Radiopacity," J Biomed Mat Res Part B: Appl Biomater, pp. 56-62 (2008).
Aunoble et al., "Biological Performance of a New Beta-TCP/PLLA Composite Material for Applications in Spine Surgery: In Vitro and in Vivo Studies," J Biomed Mat Res, 78A, pp. 416-422 (2006).
Dorozhkin, "Calcium Orthophosphate Cements for Biomedical Application," J Mater Sci, 43, pp. 3028-3057 (2008).
Habraken et al., "Ceramic Composites As Matrices and Scaffolds for Drug Delivery in Tissue Engineering," Advanced Drug Delivery Reviews, 59, pp. 234-248 (2007).
Habraken et al., "Introduction of Enzymatically Degradable Poly(trimethylene carbonate) Microspheres Into an Injectable Calcium Phosphate Cement," Biomaterials, 29, pp. 2464-2476 (2008).
Habraken et al., "Introduction of Gelatin Microspheres Into an Injectable Calcium Phosphate Cement," J Biomed Mater Res, 87A, pp. 643-655 (2008).
Kikuchi et al., "In Vitro Change in Mechanical Strength of Beta-Tricalcium Phosphate/Copolymerized Poly-L-Lactide Composites and Their Application for Guided Bone Regeneration," J Biomed Mat Res, 62, pp. 265-272 (2002).
Lewis, "Injectable Bone Cements for Use in Vertebroplasty and Kyphoplasty: State-Of-The-Art Review," J Biomed Mater Res Part B: Appl Biomater, 76B, pp. 456-468 (2006).
Lin et al., "Preparation and Evaluation of Beta-TCP/Polylactide Microspheres As Osteogenesis Materials," J Appl Polym Sci, 108, pp. 3210-3217 (2008).
Link et al., "Bone Response and Mechanical Strength of Rabbit Femoral Defects Filled With Injectable CaP Cements Containing TGF-Beta1 Loaded Gelatin Microparticles," Biomaterials, 29, pp. 675-682 (2008).

(56) References Cited

OTHER PUBLICATIONS

Link et al., "Evaluation of the Biocompatibility of Calcium Phosphate Cement/PLGA Microparticle Composites," J Biomed Mater Res, 87A, pp. 760-769 (2008).
Office Action in copending U.S. Appl. No. 13/022,771 dated Dec. 9, 2014 (Examiner Love), 13 pages.
Related U.S. Appl. No. 14/157,304, filed Jan. 16, 2014.
Rezwan et al., "Biodegradable and Bioactive Porous Polymer/Inorganic Composite Scaffolds for Bone Tissue Engineering," Biomaterials, 27, pp. 3413-3431 (2006).
Ruhe et al., "Biocompatibility and Degradation of Poly(DL-Lactic-Co-Glycolic Acid)/Calcium Phosphate Cement Composites," J Biomed Mat Res, 7aA, pp. 533-544 (2006).
Ruhe et al.; "Porous Poly(DL-Lactic-Co-Glycolic Acid)/Calcium Phosphate Cement Composite for Reconstruction of Bone Defects"; Tissue Engineering; vol. 12, No. 4; pp. 789-800 (2006).
English language abstract of JP 5-507862 A, translation of 1993 document.
English language translation of JP 64-22257, translation of 1989 document.
Machine Translation of JP 1139516 (HO6(1994)-0842898) from http://www4.ipdl.inpit.go.jp/Tokujitu/tisogodbenk.ipdl, last viewed on Jan. 22, 2009.
English-language translation of SE 8903538, "Implant material and method for the manufacture thereof," Bioapatite AB, translation of 1991 document.
Karr, Jeffrey; "Osteomyelitis and Antibiotic Beads—What Do You Think About Using Antibiotics Other Than Vancomycin or Aminoglycosides?"; podiatry.com, Aug. 22, 2009; p. 1; XP55018678; retrieved from the Internet (URL:http://www.podiatry.com/etalk/Osteomyelitis-and-antibiotic-t1045.html?section_id=20#-1), retrieved Feb. 7, 2012.

* cited by examiner

PREPARATION OF BONE CEMENT COMPOSITIONS

CROSS-REFERENCE TO RELATED APPLICATIONS

This application claims the benefit of priority U.S. Provisional Application No. 61/302,596 filed Feb. 9, 2010

BACKGROUND OF THE INVENTION

1. Field of the Invention

The present invention relates to the preparation of an injectable paste from powdery calcium sulfate based bone cement compositions and a medicament, which compositions are made ready to use, by mixing with an aqueous liquid and further to the manufacture of antibiotic beads and the use thereof for treatment of osteomyelitis.

Introduction

The life expectancy of the world population has increased tremendously during the last 50 years, and according to the forecasts there will be more people over 60 years of age than less than twenty years of age in Europe.

More people will need medical help for diseases related to age, which will increase the pressure of the hospitals.

Bone is the second most common material to be transplanted after blood. The most reliable method to repair bone defects is to use autogenous bone, i.e. bone taken from another site in the body. However, problems may occur at the second surgical site from where the graft is taken. To avoid these extra trauma allograft can be used i.e. bone graft between individuals of the same species. Allograft has a lower osteogenic capacity than autograft and the rate of new bone formation might be lower. They also have a higher resorption rate, a larger immunogenic response and less revascularisation of the recipient. Allograft must also be controlled for viruses since they can transfer, for example, HIV and hepatitis. The use of allograft is now the most common method for bone transplantation and repairing of bone defects. To solve the problems of supply, unpredictable strength and risk of infection, synthetic bone substitutes have become a realistic alternative. Thus, the demand for and use of synthetic bone substitutes is increasing rapidly.

Calcium sulfate hemihydrate, $CaSO \cdot \frac{1}{2}H_2O$, CSH, was one of the first materials investigated as a substitute for bone grafts. Calcium sulfate hemihydrate implanted in areas of subcortical bone produces no further untoward reaction in the tissue than normally is present in a fracture. The new bone growing into calcium sulfate is normal bone, and no side effects attributable to the implantation of calcium sulfate hemihydrate have been noted in adjacent tissues or in distant organs.

The most important advantage with calcium sulfate is its excellent biocompatibility. The drawbacks are the rapid resorption and low strength, which makes it less useful in larger or non-contained defects and when the fracture healing exceeds 4-6 weeks.

When calcium sulfate hemihydrate is mixed with water, it will hydrate to calcium sulfate dihydrate, CSD, according to the below reaction scheme (1):

$$CaSO_4 \cdot 0.5H_2O + 1.5H_2O => CaSO_4 \cdot 2H_2O + Heat \quad (1)$$

The hydration reaction of calcium sulfate hemihydrate can be summarized in three phases.

1) The induction period starting immediately after the calcium sulfate hemihydrate powder is mixed with water. The calcium sulfate hemihydrate then dissolves and the solution becomes supersaturated with respect to calcium and sulfate ions. This leads to precipitation of the less soluble calcium sulfate dihydrate, CSD. In order for the hydration reaction to be able to proceed, these CSD nuclei have to have a radius that is larger than a "critical radius" (determined for each specific system). The induction period is critical for the hydration reaction and any disturbances in the solubility of calcium sulfate hemihydrate or growth of CSD-crystals in this phase will delay the further hydration reaction to a higher degree than occurrence of the same disturbance in later phase of the process.

2) The acceleratory or growth period starts when a sufficient number of CSD crystals have reached the critical size for them to act as nucleating embryos. The CSD nucleus formed will then grow and form large crystals. The crystals will eventually be sufficiently large to interlock with each other and the friction between crystals contributes to the strength of the formed material.

3) The third phase is relatively slow and consists of the completion of the hydration of the calcium sulfate hemihydrate as stated in N. B. Singh and B. Middendorf, *Calcium sulphate hemihydrate hydration leading to gypsum crystallization*, Progress in Crystal Growth and Characterization of Materials 53 (2007) 57-77 and as illustrated in FIG. 1 in the form of a schematic view showing the fraction of hydrated calcium sulfate dihydrate as a function of time.

For a variety of applications, it is desired to be able to mix different additives to calcium sulfate based bone cements. Bone substitutes comprising an antibiotic content are often requested to prevent or treat osteomyelitis (bone infections) (Steven Gitelis and Gregory T. Brebach, *The treatment of chronic osteomyelitis with a biodegradable antibiotic implant*, Journal of Orthopaedic Surgery 2002 10(1): 53-60).

Several non-biodegradable and biodegradable antibiotic cement delivery systems are available for the delivery of antibiotics for adjunctive therapy in the management of osteomyelitis. A major representative of the non-biodegradable delivery system includes the polymethyl methacrylate (PMMA) beads. Antibiotics that can be incorporated into this delivery system are however limited to the heat stable antibiotics such as vancomycin and the amino glycosides; tobramycin being the more popular.

However, it has been found that addition of various additives such as bioactive agents, e.g. an antioxidant, a vitamin, a hormone, antibiotics a cytostatic, a bisphosphonate, a growth factor, or a protein or peptide or a bone marrow aspirate or demineralised bone, to bone cement compositions based on calcium sulfate hemihydrate often interferes with or even prevents the hardening process thereof. The retarding effect on the hardening has been found to be dependent of the identity of the additive and the specific bone mineral substitute composition.

Thus it has been found (Steven Gitelis and Gregory T. Brebach, ibid) that addition of antibiotics may retard or accelerate the hydration of calcium sulfate hemihydrate into calcium sulfate dihydrate significantly, or even prevent completion of the hydration and consequently, the hydraulic cement may no longer be suitable for use in clinical applications since its properties are significantly changed by the addition of the antibiotic. The incomplete/slow CSH hydration affects different properties of the final material and excludes a number of applications for the material.

2. Description of the Related Art

Various bone cement compositions comprising ceramics hardening in vivo upon contact with water or body fluids and comprising a medicament have been disclosed.

WO 2004/078223 (Lidgren) discloses a bone mineral substitute material comprising a calcium phosphate component and hardened calcium sulphate and an additive such as an antioxidant, a vitamin, a hormone, an antibiotic, a cytostatic, a bisphosphonate, a growth factor, or a protein. The additive can be included in the particulate hardened calcium sulfate during its preparation or included in the sterile aqueous liquid of the composition, and in the experiments a slow release of iohexyl or gentamycin was found when the additive was included in the particulate hardened calcium sulfate during its preparation.

In N. B. Singh and B. Middendorf, *Calcium sulphate hemihydrate hydration leading to gypsum crystallization*, Progress in Crystal Growth and Characterization of Materials 53 (2007) 57-77 it is disclosed that the presence of e.g. carboxylic acids retards the growth of gypsum crystals during hemihydrate hydration.

Richelsoph et al, *Elution Behavior of Daptomycin-loaded Calcium Sulfate Pellets*, CLINICAL ORTHOPAEDICS AND RELATED RESEARCH, Number 461, pp 68-73, found that antibiotics often tend to disturb the setting of calcium sulphate hemihydrate and that when adding daptomycin the CSH did not harden, and incorporation of traditional accelerant techniques (addition of a small percentage of calcium sulphate dihydrate, addition of saline, increasing the temperature and decreasing the water content) all failed to improve the setting characteristics. Furthermore, Richelsoph found that when using potassium sulfate as accelerator a suitable pellet was produced and describes a two-step method in which calcium sulfate hemihydrate powder and a potassium sulfate solution were stirred vigorously for two minutes and allowed to rest for additionally one minute before daptomycin was added.

The hydration of calcium sulfate hemihydrate, CSH, into calcium sulfate dihydrate, CSD, may be retarded or prevented from being completed. This may lead to the result that the hydraulic cement will no longer be suitable for use in clinical applications since its properties are significantly changed by addition of an antibiotic. The incomplete/slow CSH hydration affects different properties of the final material and excludes the use of such a material for a number of applications. Accelerated hydration has also been reported when adding antibiotics, which leads to similar limitations.

WO 02/05861 discloses an injectable composition for a bone mineral substitute material, which comprises a dry powder mixed with an aqueous liquid, said powder comprising a first reaction component comprising a calcium sulphate hemihydrate with the capability of being hardened to calcium sulphate dihydrate when reacting with said aqueous liquid; a second reaction component, which comprises a calcium phosphate with the capability of being hardened to a calcium phosphate cement when reacting with said aqueous liquid; and at least one accelerator for the reaction of said first and/or second reaction component with said aqueous liquid. WO 02/05861 does not disclose any specific compositions comprising an additive having a retarding effect on the hardening of the inorganic bone mineral substitute composition when admixed together with an aqueous liquid or any measure to counteract such retardation of the hardening of the composition.

U.S. Pat. No. 6,251,139 discloses a method of using a plaster of Paris as an orthopedic filling material prepared by mixing 15-80% by weight of calcium sulfate half-hydrate and 85-20% by weight of water, an aqueous solution, an aqueous dispersion, or an aqueous suspension; and stirring the resulting mixture into a paste having a viscosity in the range of 20 and 75 poises. The paste is injected into a cavity of a bone or a vertebra to be reinforced. U.S. Pat. No. 6,251,139 discloses addition of drugs or nutrients before the mixing or in the midst of the mixing such that they are mixed with the calcium sulfate half-hydrate and water, the aqueous solution, the aqueous dispersion or the aqueous suspension provided. Further it is stated that such drugs and nutrients added should not have adverse effect on the hardening of the paste. After mixing the resulting paste is rested for a period of time to have a desired viscosity.

It is an object of the invention to provide an inorganic bone mineral substitute composition comprising an additive having a desired effect, said additive having a retarding or strong retarding effect on the hardening of the inorganic bone mineral substitute composition when admixed together with an aqueous liquid for hardening of the cement composition without sacrificing the rate of setting, the completion of the hydration of CSH into CSD or the properties of the final product (after 30 minutes) which is important for the clinical use thereof and of special importance in environments having a high blood flow to reduce the risk of leakage and risk of ingress in the blood vessels, which may cause an embolus.

It is also an object of the invention to provide an inorganic bone mineral substitute composition comprising an additive having a desired effect, said additive having a retarding effect on the hardening of the inorganic bone mineral substitute composition without changing the composition of bone mineral substitute by adding further chemicals.

It is a further object of the invention to provide an inorganic bone mineral substitute composition comprising an additive having a desired effect, said additive having, as a side effect, a retarding or strong effect on the hardening of the inorganic bone mineral substitute composition which may be applied shortly after mixing without delay which would else prolong the time needed for surgery and thus the occupancy of the operating room reducing the total capacity thereof and the potentially dangerous period under anaesthesia.

SUMMARY OF THE INVENTION

The present invention relates in a first aspect to a method for the preparation of ready-to-use injectable bone cement paste compositions by mixing a dry inorganic bone cement powder comprising a particulate calcium sulfate hemihydrate capable of hardening in vivo by hydration of the calcium sulfate hemihydrate forming calcium sulfate dihydrate, an aqueous liquid and an additive, said additive having a retarding effect on the hardening of the inorganic bone mineral substitute composition when admixed together with an aqueous liquid, said method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component, b) mixing the bone cement powder with the aqueous liquid for a period of time, c) leaving the mixture for the time needed for allowing the hydration reaction of the calcium sulfate hemihydrate to proceed and allowing calcium sulfate dihydrate crystals to form and grow, and d) admixing the additive by means of a short-duration mixing using a minimum of energy.

In a second aspect the invention relates to a method of prophylactic or therapeutic treatment of a disorder related to supportive tissues in a human or non-human animal subject, which method comprises providing to said subject a composition for an injectable inorganic bone mineral substitute paste material with the capability of being hardened in a body fluid in vivo by hydration of calcium sulfate hemihydrate forming calcium sulfate dihydrate, said composition comprising a dry inorganic bone cement powder composition comprising particulate calcium sulfate hemihydrate, an aqueous liquid and at least one bioactive agent active against said disorder, said bioactive agent having a retarding effect on the hardening of the inorganic bone mineral substitute composition when admixed together with an aqueous liquid, said method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component,
b) mixing the bone cement powder with the aqueous liquid for a period of time
c) leaving the mixture for the time needed for allowing the hydration reaction of the calcium sulfate hemihydrate to proceed and allowing calcium sulfate dihydrate crystals to form and grow, and
d) admixing the additive by means of a short-duration mixing using a minimum of energy and
e) introducing the resulting inorganic bone mineral substitute material into said tissue.

In a third aspect the invention relates to a method of implanting a hardened inorganic bone mineral substitute in the form of hardened pellets, small beads, rods, or blocks to a supportive tissue in a human or non-human animal subject, said pellets comprising an additive having a retarding effect on the hardening of the inorganic bone mineral substitute composition when admixed together with an aqueous liquid, said hardened inorganic bone mineral substitute being prepared by a method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component,
b) mixing the bone cement powder with the aqueous liquid for a period of time,
c) leaving the mixture for the time needed for allowing the hydration reaction of the calcium sulfate hemihydrate to proceed and allowing calcium sulfate dihydrate crystals to form and grow, and
d) admixing the additive by means of a short-duration mixing using a minimum of energy and
e) introducing the resulting inorganic bone mineral substitute material into said tissue.

In a fourth aspect the invention relates to a method of concomitant implanting an inorganic bone mineral substitute to a supportive tissue in a human or non-human animal subject and prophylactic or therapeutic administration of an antibiotic agent, wherein a hardened inorganic bone mineral substitute material is introduced into said tissue, said antibiotic agent having a retarding effect on the hardening of the inorganic bone mineral substitute composition when admixed together with an aqueous liquid, said hardened inorganic bone mineral substitute material being prepared by a method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component,
b) mixing the bone cement powder with the aqueous liquid for a period of time,
c) leaving the mixture for the time needed for allowing the hydration reaction of the calcium sulfate hemihydrate to proceed and allowing calcium sulfate dihydrate crystals to form and grow, and
d) admixing the antibiotic agent,
e) forming the resulting material into pellets, small beads, rods or blocks and allowing these to harden ex vivo and
f) introducing the resulting hardened inorganic bone mineral substitute material into said tissue.

In a fifth aspect the invention relates to an injectable paste composition comprising a particulate calcium sulfate hemihydrate capable of hardening in vivo by hydration of the calcium sulfate hemihydrate forming calcium sulfate dihydrate, an aqueous liquid and a bioactive agent, said bioactive agent having a retarding effect on the hardening of the inorganic bone mineral substitute composition when admixed together with an aqueous liquid, said paste being prepared by a method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component, wherein the calcium phosphate component is hydroxyl apatite in an amount of 30 to 50 wt % of the dry powder or tricalcium phosphate,
b) mixing the bone cement powder with the aqueous liquid for a period of time
c) leaving the mixture for the time needed for allowing the hydration reaction of the calcium sulfate hemihydrate to proceed and allowing calcium sulfate dihydrate crystals to form and grow, and
d) admixing the bioactive agent, for use as a medicament for prophylactic or therapeutic treatment of a disorder related to supportive tissues in a human or non-human animal subject, which method comprises local administration to said subject, preferably by injection, of said composition comprising a prophylactic or therapeutic amount of said at least one bioactive agent, which is released from said composition, optionally while systemically and/or concomitantly administrating a prophylactic or therapeutic amount of at least one bioactive agent.

BRIEF DESCRIPTION OF THE DRAWINGS

The invention is disclosed more in detail with reference to the drawings in which FIG. 1 Shows a schematic view of the fraction of hydrated CSH as a function of time,
FIG. 4A shows the mixing of an iohexol solution with Cerament™ Bone Void Filler.
FIG. 4B shows the io hexol/Cerament™ Bone Void Filler mixture being placed in a sterile bowl.

FIG. 4C shows the addition of Vancomycin to the iohexol/Cerament™ Bone Void Filler mixture.

FIG. 4D shows the placement of the iohexol/ Cerament™ Bone Void Filler/Vancomycin mixture in the bead mold.

FIG. 4E shows the final antibiotic beads.

DETAILED DESCRIPTION OF THE PRESENT INVENTION

Figure 1:
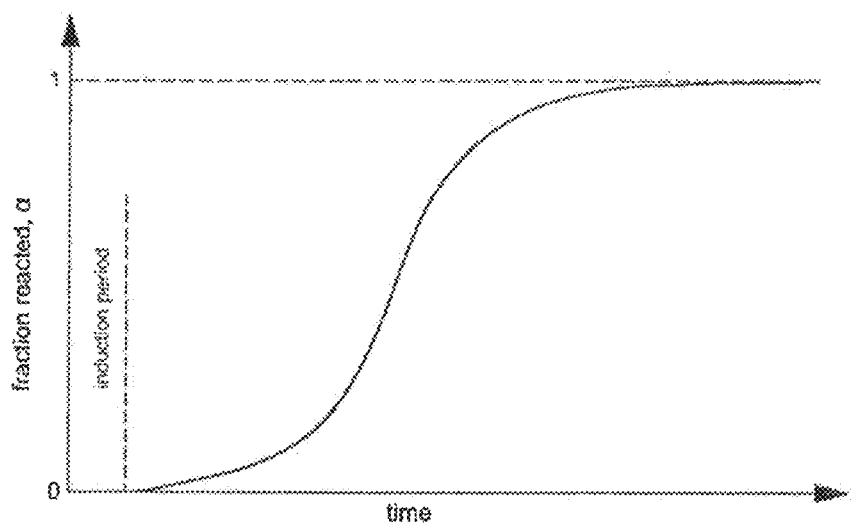

The present invention relates to a method for the preparation of ready-to-use injectable bone cement paste compositions by mixing a dry inorganic bone cement powder comprising a particulate calcium sulfate hemihydrate capable of hardening in vivo by hydration of the calcium sulfate hemihydrate forming calcium sulfate dihydrate, an aqueous liquid and an additive, said additive having a retarding effect on the hardening of the inorganic bone mineral substitute composition when admixed together with an aqueous liquid, said method comprising
a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component
b) mixing the bone cement powder with the aqueous liquid for a period of time,
c) leaving the mixture for the time needed for allowing the hydration reaction of the calcium sulfate hemihydrate to dissolve at least partially and formation of calcium sulfate dihydrate crystallization nuclei, and
d) admixing the additive by means of a short-duration mixing using a minimum of energy.

The resulting material may be introduced to a supportive tissue in a human or non-human animal subject directly by injection and allowed to harden in vivo or it may shaped into a desired shape such as pellets, small beads, rods, or blocks and left for hardening ex vivo and then be introduced to the supportive tissue. In the alternative the resulting paste material may be manually moulded and introduced into the supportive tissue and shaped in place and then allowed to harden in vivo.

Supportive tissue may be any part of the tissue supporting the body or functional parts thereof such as bone tissue.

In the present context the expressions "harden" and hardened" are used to designate setting reaction taking place when hydraulic cements react with water.

It has been found that the method used to mix calcium sulfate based bone substitutes with an additive is crucial for the properties of the materials. This is especially relevant when adding certain additives that retard the setting process. It has now surprisingly been found that the time of addition of the additive in the preparation of CSH-based bone cement has a significant effect on the setting process.

It has now surprisingly been found that when pre-mixing a hydraulic cement powder comprising powdered CSH and CSD as an accelerator and a powdered calcium phosphate component with the aqueous liquid to be used for preparing the cement and allowing the hydration reaction of the CSH start before adding the additive, it is possible to shorten the setting times for the cement comprising the additive to the level observed in the absence of the additive and to obtain a complete hydration of CSH to CSD without having to substitute usually preferred accelerators and without having to mix under vigorous stirring which would require the use of separate mixing equipment in the sterile operating rooms.

The delayed mixing technique permits the calcium sulfate hydration process to proceed and allow the formation of calcium sulfate dihydrate crystallization nuclei prior to addition of an agent which can potentially alter the setting behavior and prolong the setting time.

The retarding effect of the added agent is reduced by letting the hydration process start and proceed and allow the calcium sulphate dihydrate crystals have time to form and to grow before addition of the agent.

Most retarding agents act on the formation of the calcium sulfate dihydrate crystals, i.e. prevents the formation of these crystals. If time is given to the material to form these crystals before addition of the retarding agent it has been found that the retarding effect of the agent is decreased.

Examples of retarding agents that could be desirable to add to such material for the application in human or animal bodies are: Vitamin E (an antioxidant which facilitates bone regeneration, bone marrow aspirate (contains osteogenic factors), demineralized bone matrix (contains bone morphogenic proteins), antibiotics (for preventing/treating infections) and cytostatics (for treatment of bone malignancy).

In accordance with the present invention it is possible to avoid changing the composition of bone mineral substitute by adding further chemicals (which may have undesired adverse effects) in order to counteract a retarding effect of a specific desired additive, and furthermore, the bone mineral substitute may be applied immediately after mixing without delay.

It is believed that allowing the calcium sulfate hemihydrate to dissolve at least partially will lead to formation of calcium sulfate dihydrate crystallization nuclei, which will ensure the proceeding of the hardening. The mixing may be carried out manually in a mixing tool which then also can serve as injection syringe.

The time needed for the hydration reaction to start depends on the length of the induction period for the particular system and it easily determined for each system by the skilled in the art by routine experiments. An initial mixing time of 10 seconds to 5 minutes, preferably from about 20 seconds to 2 minutes, most preferred about 30 seconds has been found suitable when carrying out the present invention. After the mixing, the material is suitably left for at least 15 seconds, depending on the initial mixing, preferably >1 minute before addition of additive.

These time windows also leave a sufficiently broad time span for the use of the resulting paste to absorb many unforeseen incidents or minor delays often occurring during surgery and does not cause unnecessary prolongation of the surgery.

The calcium sulfate hemihydrate may be α or β-calcium sulfate hemihydrate, α-calcium sulfate hemihydrate being preferred, and suitably the powdered calcium sulfate hemihydrate has a particle size of less than 500 μm, preferable less than 100 μm and preferable 99% of the particles have a particle size less than 80 μm.

The particle size of the powdered calcium sulfate dihydrate accelerator suitably is less than 500 μm, preferably less than 150 μm, and most preferable less than 100 μm.

The particulate calcium sulfate dihydrate should be present in an amount between 0.1 and 10 wt %, preferably between 0.1 and 2 wt % of the calcium sulfate hemihydrate which is to react with the aqueous liquid The powdered calcium phosphate component may e.g. be amorphous calcium phosphate (ACP), monocalcium phosphate monohydrate (MCPM; $Ca(H_2PO_4)_2 \cdot 2H_2O$), dicalcium phosphate dihydrate DCPD (brushite; $CaHPO_4 \cdot 2H_2O$), octacalcium phosphate ($Ca_8(HPO_4)_2(PO_4)_4 \cdot 5H_2O$), calcium deficient hydroxyl apatite (CDHA; $Ca_9(HPO_4)(PO_4)_5(OH)$), tricalcium phosphate (TCP; $Ca_3(PO_4)_2$), and hydroxyl apatite (HA; $Ca_{10}(PO_4)_6(OH)_2$.

It is preferred that the powdered calcium phosphate component is hydroxyl apatite or tricalcium phosphate, preferably hydroxyl apatite or α-tricalcium phosphate having a particle size less than 100 μm.

When the powdered calcium phosphate component is tricalcium phosphate it is suitable to add an accelerator known per se such as hardened particulate calcium phosphate or disodium hydrogen phosphate as an accelerator for the calcium phosphate component. The hardened calcium phosphate should have a particle size which is less than 100 μm, suitably less than 50 μm, and comprise between 0.1 and 10 wt %, preferably between 0.5 and 5 wt % of the calcium phosphate which is to react with an aqueous liquid.

The reaction of calcium phosphate to a calcium phosphate cement can also be accelerated by addition of a phosphate salt, for example disodium hydrogen phosphate ($Na_2HPO_4$), which may be added as dry particles or dissolved in the aqueous liquid. In this case, the accelerator should be present in the aqueous liquid at concentrations of 0.1-10 wt %, preferably 1-5 wt %.

In order to confer an initial strength to an inorganic bone mineral substitute material the calcium sulphate hemihydrate should comprise 2-80 wt %, preferably 10-30 wt % of the dry powder to be mixed with an aqueous liquid, when a calcium phosphate to be hardened is used. Likewise, the calcium phosphate to be hardened to a calcium phosphate cement should comprise 20-98 wt %, preferably 70-90 wt % of the dry powder. When using hydroxyl apatite as the calcium phosphate component, the hydroxyl apatite suitably comprises from 30 to 50 wt % of the dry powder, preferably about 40 wt %, in which case the CSH+CSD will constitute from 50 to 70 wt % of the dry powder, preferably about 60 wt %. In the composition, the aqueous liquid should comprise between 0.1 and 2 ml, preferably between 0.2 and 0.7 ml per gram powder.

An inorganic bone cement powder which may suitably be used in the method of the present invention is commercially available from BONE-SUPPORT AB, Lund, Sweden under the trade name CERAMENT™ BONE VOID FILLER.

In a preferred embodiment of the invention the additive is in the form of a bioactive agent.

An additive in the form of a bioactive agent may e.g. be an antioxidant, a vitamin, a hormone, an antibiotic, a cytostatic, a bisphosphonate, a growth factor, or a protein or peptide. The additive may also be a bone marrow aspirate or demineralised bone. Advantageously, the additive is a substance that induces, stimulates and/or accelerates bone formation, such as osteoinductive compounds and/or compounds reducing bone turn over.

Suitable bone inducing substances, which stimulate and/or accelerate bone formation, are growth factors and hormones. Growth factors and derivatives thereof are preferred, which are locally acting.

It is preferred to use growth factors, which are autologous and effective in connection with bone, tendon or cartilage. Such growth factors are for example transforming growth factor (TGF β3), bone morphogenic protein (BMP-2 or BMP-7), PTHrP, osteoprotegrin (OPG), Indian Hedgehog, RANKL, basic fibroblast, insulin-like growth factor (IgF-1 or IGF-2), platelet derived growth factors, and vascular growth factors. These endogenously produced growth factors may be used as an additive either as single entities or combined in a growth factor mixture in order to accelerate bone growth. Thus, it is preferred that an endogenously produced bioactive molecule is used as a substance that induces bone formation.

Examples of other bone stimulating compounds are parathyorid hormones and derivatives thereof, estrogens, progesterones, androgens, testosterones, calcitonin, somatomedin, and oxytocin, preferably also autologous, but they can also be produced according to procedures known within the art.

The enamel matrix proteins amelin-1, amelin-2 and ameloblastin can also be included as an additive. Such compounds may either be autologous or extracted from or produced by tissues or cells from other species, or synthetically produced or produced by other living cells or organisms.

Likewise, the cholesterol-lowering compound statin can also be included in order to induce, stimulate and/or accelerate bone formation.

Examples of suitable bone breakdown inhibitors are biphosphonates, osteocalcin, osteonectin and derivatives thereof, which can be included as an additive in the particulate calcium sulfate of the inventive composition and of the resulting substitute.

The bioactive agent can also be an anti-infectious substance, i.e. a compound with a static or cidal effect against invading foreign living material.

Such compounds include natural antibiotics as well as other semisynthetic and synthetic antibacterial or bacteriostatic compounds, which are acting against pathogenic and/or infectious microorganisms, e.g. staphylococci. Examples of antibiotics for bone infections are tetracycline-HCl, vancomycin, tobramycin, gentamycin, and cephalosporin.

Cytostatic agents, such as cis-platinum, ifosfamide, methotrexate, doxorubicin-HCl, arsenic trioxide, and retinoids or derivatives thereof can also be used as a bioactive agent. The bioactive agent can in a similar way be an antiviral compound, an antifungal compound, a tuberculostatic or tuberculocidal compound or an antiparasite compound.

In a preferred embodiment the bioactive agent is an antibiotic agent.

In the method of the invention further additives known per se for controlling the rheological properties, e.g. biocompatible oils as described in applicant's WO 01/76649, may also be added in a concentration of more than 1 wt % but less than 10 wt % of the total weight of the composition in order to improve the rheology of the same. Preferably, the concentration of oil should be between 2 and 6 wt % of the total weight of the composition, and such addition is also considered an aspect of the present invention.

It is also considered an aspect of the present invention to add an X-ray contrast agent known per se, preferably a non-ionic water soluble contrast agent such as iohexyl as described in applicant's WO 03/053488.

The invention further relates to a method of prophylactic or therapeutic treatment of a disorder related to supportive tissues in a human or non-human animal subject, which method comprises providing to said subject an injectable paste composition for an inorganic bone mineral substitute material with the capability of being hardened in a body fluid in vivo by hydration of calcium sulfate hemihydrate forming calcium sulfate dihydrate, said composition comprising a dry inorganic bone cement powder composition comprising particulate calcium sulfate hemihydrate, an aqueous liquid and at least one bioactive agent active against said disorder, said bioactive agent having a retarding effect on the hardening of the inorganic bone mineral substitute composition when admixed together with an aqueous liquid, said method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component b) mixing the bone cement powder with the aqueous liquid for a period of time, c) leaving the mixture for the time needed for allowing the hydration reaction of the calcium sulfate hemihydrate to proceed and allowing calcium sulfate dihydrate crystals to form and grow, and d) admixing the additive by means of a short-duration mixing using a minimum of energy and e) introducing the resulting inorganic bone mineral substitute material into said tissue.

The disclosure concerning suitable and preferred embodiments stated above in connection with the explanation of the method for the preparation of a ready-to-use bone cement composition applies mutatis mutandum for this aspect of the invention.

Furthermore the invention relates to a method of implanting a hardened inorganic bone mineral substitute in the form of hardened pellets, small beads, rods, or blocks to a supportive tissue in a human or non-human animal subject, said pellets comprising an additive having a retarding effect on the hardening of the inorganic bone mineral substitute composition when admixed together with an aqueous liquid, said hardened inorganic bone mineral substitute being prepared by a method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component b) mixing the bone cement powder with the aqueous liquid for a period of time, c) leaving the mixture for the time needed for allowing the hydration reaction of the calcium sulfate hemihydrate to proceed and allowing calcium sulfate dihydrate crystals to form and grow, and d) admixing the additive by means of a short-duration mixing using a minimum of energy and e) introducing the resulting inorganic bone mineral substitute material into said tissue.

The mixture can be introduced to a bone defect by injection or moulded and inserted manually.

In one embodiment the invention relates to the use of a paste according to the invention for producing antibiotic beads for treatment of osteomyelitis.

The disclosure concerning suitable and preferred embodiments stated above in connection with the explanation of the method for the preparation of a ready-to-use bone cement composition applies mutatis mutandum for this aspect of the invention.

Still further the invention relates to a method of concomitant implanting an inorganic bone mineral substitute to a supportive tissue in a human or non-human animal subject and prophylactic or therapeutic administration of an antibiotic agent, said antibiotic agent having a retarding effect on the hardening of the inorganic bone mineral substitute composition when admixed together with an aqueous liquid, wherein a hardened inorganic bone mineral substitute material is introduced into said tissue, said hardened inorganic bone mineral substitute being prepared by a method comprising a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component b) mixing the bone cement powder with the aqueous liquid for a period of time, c) leaving the mixture for the time needed for allowing the hydration reaction of the calcium sulfate hemihydrate to proceed and allowing calcium sulfate dihydrate crystals to form and grow, and d) admixing the antibiotic agent, e) forming the resulting material into pellets, small beads, rods, or blocks and allowing these to harden ex vivo and f) introducing the resulting hardened inorganic bone mineral substitute material into said tissue.

The hardened material may be provided threaded on a string of a non-bioresorbable or bioresorbable material such as polylactide or polyglycol.

The disclosure concerning suitable and preferred embodiments stated above in connection with the explanation of the method for the preparation of a ready-to-use bone cement composition applies mutatis mutandum for this aspect of the invention.

Yet further the invention relates to an injectable paste composition comprising a particulate calcium sulfate hemihydrate capable of hardening in vivo by hydration of the calcium sulfate hemihydrate forming calcium sulfate dihydrate, an aqueous liquid and a bioactive agent, said bioactive agent having a retarding effect on the hardening of the inorganic bone mineral substitute composition when admixed together with an aqueous liquid, prepared by a) providing a bone cement powder comprising calcium sulfate hemihydrate, an accelerator for the hardening of the calcium sulfate hemihydrate by hydration, said accelerator being selected from the group consisting of saline and calcium sulfate dihydrate, and a powdered calcium phosphate component, wherein the calcium phosphate component is hydroxyl apatite in an amount of 30 to 50 wt % of the dry powder or tricalcium phosphate, b) mixing the bone cement powder with the aqueous liquid for a period of time c) leaving the mixture for the time needed for allowing the hydration reaction of the calcium sulfate hemihydrate to proceed and allowing calcium sulfate dihydrate crystals to form and grow, and d) admixing the bioactive agent, for use as a medicament for prophylactic or therapeutic treatment of a disorder related to supportive tissues in a human or non-human animal subject, which method comprises local administration to said subject, preferably by injection, of said composition comprising a prophylactic or therapeutic amount of said at least one bioactive agent, which is released from said composition, optionally while systemically and/or concomitantly administrating a prophylactic or therapeutic amount of at least one bioactive agent.

The disclosure concerning suitable and preferred embodiments stated above in connection with the explanation of the method for the preparation of a ready-to-use bone cement composition applies mutatis mutandum for this aspect of the invention.

The use according to this aspect of the invention is preferably for prophylactic or therapeutic treatment of a disorder related to supportive tissues involves fracture healing; insertion of prosthetic implants and implants of foreign materials in connection with fractures, skeletal defects, and osteotomy; non-instrumental non-invasive or invasive fusion surgery in connection with the spine or joints, preferably finger joints, vertebral joints and shoulder joints; prosthetic revision surgery; plastic surgery; reconstruction surgery; cosmetic surgery; sternotomics; trauma surgery; cancer surgery; oro-maxillar surgery; periodontitis; filling of maxillar, frontal, ethmoidal and spheroidal sinuses; creating room for an inflatable balloon or a metal expander; and infections or infestations in the musculoskeletal system, preferably osteomyelitis caused by bacteria.

Description of the Preferred Embodiments

The invention is now explained more in detail with reference to below Examples and the drawings explaining preferred embodiments of the invention.

Materials and Methods

The ceramic bone substitute specimen contained 18.5 grams powder consisting of 59.6 wt % α-CSH, 0.4% CSD and 40 wt % hydroxyl apatite. Vancomycin Hydrochloride from NordMedica Iohexyl solution comprising 180 mg I/ml was used.

Gillmore needles were used for characterization of setting time according to ASTM C266-04. The initial needle had a diameter of 2.12±0.05 mm and a weight of 113±0.5 g. The final needle had a diameter of 1.06±0.05 mm and a weight of 453.6±0.5 g.

After mixing the paste was transferred into three moulds to form the test specimens. The initial and final setting time was taken as a mean value of the three tests.

The initial setting time (IST) is the time from the moment liquid is added to the bone substitute powder until the initial needle leaves no mark on the surface of the specimen. The initial setting time shall be sufficiently long to enable injection of the bone cement paste into a void or to mould and manually apply a mouldable paste into a void. A suitable initial setting time is about 5-20 minutes. The final setting time is the time required for the paste to set so much that the final needle leaves no mark on the surface. The final setting time should preferably not exceed about 45 minutes in order to avoid inadvertent later moulding or ensuing dislocation of the paste which might cause damages on e.g. nerves or blood vessels.

Qualitative and Quantitative phase analysis was performed using the Rietveld Method using a STOE θ/θ Diffractometer (X-ray Diffraction (XRD).

Figure 3:
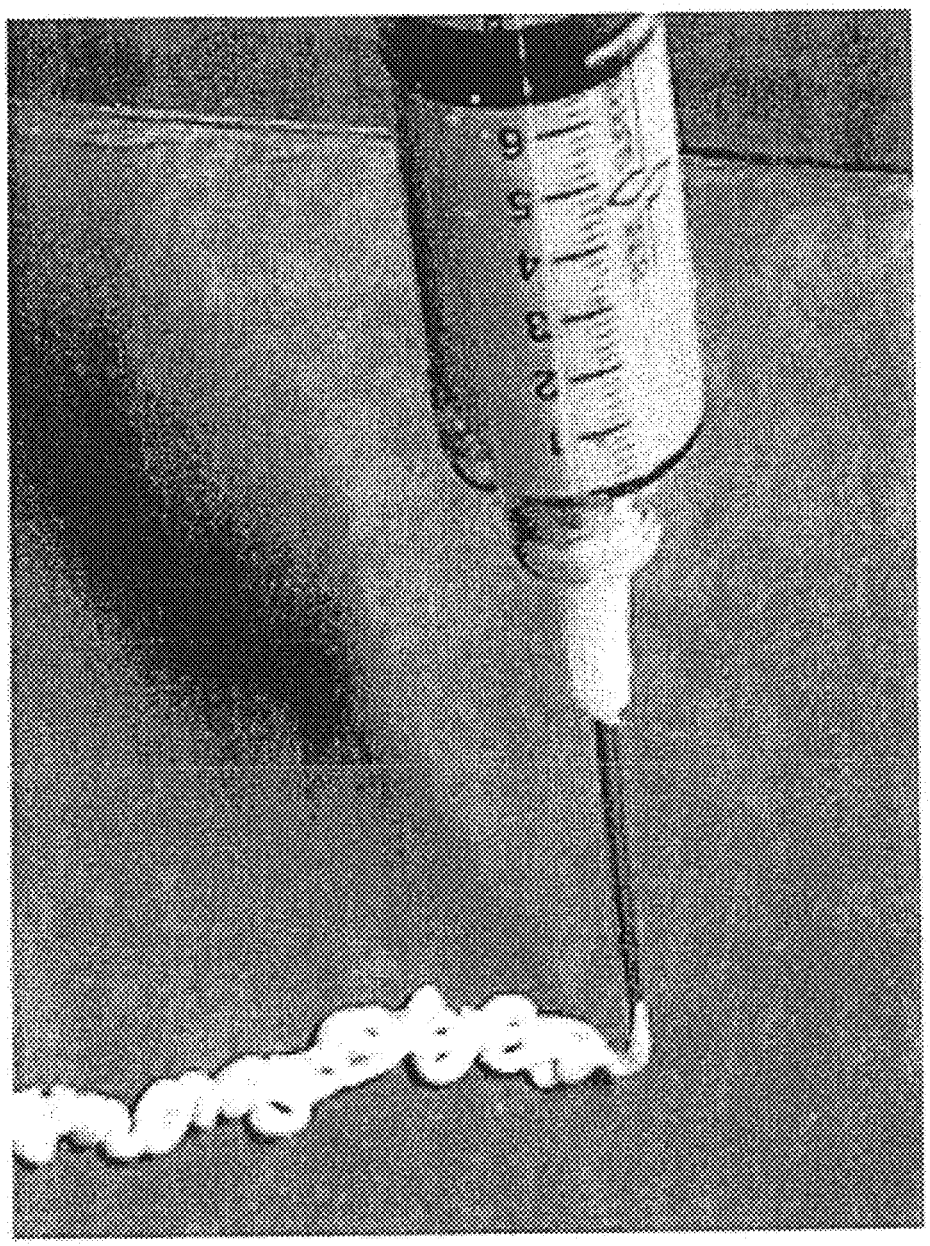
FIG. 3 shows a photograph illustrating injection test.

Injection test was performed using a 10 ml syringe with a 16 gauge needle by extruding out an approximately 5-10 cm string manually as shown in FIG. 3 each minute until the time where no bone cement could be extruded.

Example 1 and Reference Examples 1 and 2

Preparation of a ceramic bone substitute paste from 18.5 grams powder and 8 ml iohexyl solution and 1 gram Vancomycin Hydrochloride from NordMedica (5.4 wt % vancomycin of powder weight).

In Examples 1 and reference Example 1 two groups of materials having the same composition, i.e. 1 gram vancomycin, 18.5 grams specimen of ceramic bone substitute powder and 8 ml iohexyl solution, were prepared, and the only difference between Example 1 and reference Example 1 was the method of mixing the materials.

In reference Example 2 a corresponding material without vancomycin was prepared. This material corresponds to a state of the art cement paste without antibiotic.

Reference Example 1

Preparation of a Ceramic Bone Substitute Paste 1 gram vancomycin powder was first dissolved in 8 ml iohexyl solution and then the resulting antibiotic-containing liquid was mixed with 18.5 grams powder for 30 s using a mixer of the kind disclosed in WO 2005/122971. The paste was used to prepare samples for characterization according to ASTM C266-04 and for XRD measurements.

Example 1

Preparation of a Ceramic Bone Substitute Paste According to the Invention (Delayed Addition)

18.5 grams ceramic bone substitute powder and 8 ml iohexyl solution were first mixed for 30 s using the mixer stated above in the absence of the vancomycin and thereafter transferred to a bowl. At 5 min 1 gram Vancomycin powder without lumps was added to the bowl and thereafter mixed manually with the pre-mixed paste with minimal extra energy using a spatula. The paste was immediately used to prepare samples for setting characterization according to ASTM C266-04 and for XRD measurements. Injection test was performed.

Reference Example 2

Preparation of a Ceramic Bone Substitute Paste without Vancomycin 18.5 grams powder and 8 ml iohexyl solution were mixed for 30 s using the above mixer. The paste was used to prepare samples for setting characterization according to ASTM C266-04 and for XRD measurements. Injection test was performed.

Results

The results are summarized in the below Table 1.

The setting time measurements showed that the vancomycin-containing pastes prepared by dissolution of the Vancomycin powder in the liquid prior to the mixing with the hydraulic cement powder in reference Example 1 did not reach the initial setting time within the first 4.5 hours. The material finally became hard, but this is assumed to be due to drying.

In contrast to this, the vancomycin-containing paste prepared according to Example 1 gave much shorter setting times. By using this method, the initial setting time occurred in about 12 minutes and the final setting time in about 17 minutes. These setting times were quite similar to the ones obtained for the sample without vancomycin prepared according to Reference Example 2 (intial setting time about 8 minutes and final setting time at about 15 minutes).

TABLE 1

Results from setting time measurements and XRD analyses

|  | Example | Reference Example 2 without medicament (reference) | Reference Example 1 (initial addition) | Example 1 (delayed addition) |
|---|---|---|---|---|
| Setting time | Initial setting time | 8.2 ± 0.9 min | >4.5 h | 12.1 ± 2.7 min |
|  | Final setting time | 14.9 ± 1.0 min | >4.5 h | 17.3 ± 3.7 min |

TABLE 1-continued

Results from setting time measurements and XRD analyses

| Example | | Reference Example 2 without medicament (reference) | Reference Example 1 (initial addition) | Example 1 (delayed addition |
|---|---|---|---|---|
| Phases in dry sample | Amount of CSD | 56.2 ± 1.2 wt % | 38.3 ± 1.0 wt % | 58.5 ± 1.3 wt % |
| | Remaining amount of CSH | 3.3 ± 0.6 wt % | 20.2 ± 0.9 wt % | 3.1 ± 0.4 wt % |
| Injection time through 16 gauge needle | | Possible until 6 min. | Possible >1 hour | Possible until 11 min. |

Minimum one sample was tested in each Example

Figure 2:
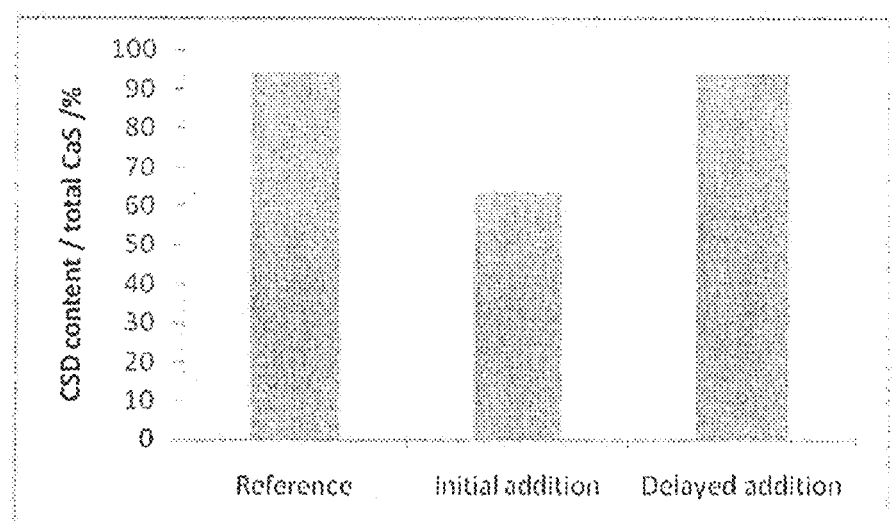
FIG. 2 shows to what extent the CSH was converted to CSD in three samples.

In FIG. 2 is shown to what extent the CSH was converted to CSD in the three samples. The figures stated are the weight percentage of the CSD of the total amount of calcium sulfate The XRD results stated in table 1 and FIG. 2 shows that the CSH in the sample prepared in reference Example 1 was only hydrated to about ⅔.

This supports the assumption that the hardening of the cement in this case is partly due to simple drying of the mix and not completely due to setting.

For the reference sample of Reference Example 2 and the sample prepared in Example 1, the XRD results showed that an almost complete CSH conversion to CSD.

Discussion

The results obtained using the method according to the invention indicates that it is generally applicable for the admixing of a wide range of different additives such as bioactive agents to calcium sulfate based compositions in which a hardening of calcium sulfate hemihydrate to calcium sulfate dihydrate is to take place.

Although it is possible to promote the dissolution of CSH and speed up the setting process, for example by adding further accelerators such as NaCl it is, however, in many applications, important not to change the chemical composition of the material and hence, addition of other chemicals should thus be avoided.

The present invention shows a drastic effect on the final properties of the material is obtained.

It was found that an important factor for affecting the setting times in the method of the invention is the mixing of the cement with the additive. It was found that it is important that this mixing is a short-duration mixing using a minimum of energy. The more energy that is used, the less viscous will the paste be and the advantage of using the method of the invention may be lost. A slow gentle manual mixing using a broad spatula has been found to be suitable for the purpose of the present invention and constitutes a presently preferred embodiment.

When the bone cement paste is to be injected directly into a void it is very important to be able to control how the antibiotic addition is affecting the hardening properties of the paste. This is especially pertinent in environments having a high blood flow as a very slow setting of the paste will increase the risk for leakage of the material.

By using the method of the invention it was possible to shorten the setting times from >4.5 h down to approximately 12 min (IST: 12.1±2.7 min) when adding vancomycin to a bone cement paste. The method also gave a complete hydration of CSH to CSD.

Example 3

In an analogous manner as described in Reference Example 1 pastes comprising calcium sulfate hemihydrate and calcium sulfate dihydrate as accelerator for the hardening thereof as well as hydroxyl apatite and iohexyl and further comprising bone morphogenic protein or various antibiotics were prepared. The pastes were used to prepare samples for setting characterization according to ASTM C266-04. The results of the determination of the effect of delayed addition on the initial setting time (IST) are summarized in the below Table 2 together with results obtained from samples prepared using initial addition. The results are mean values of three determinations.

TABLE 2

Effect of additives on setting time

| Additive | Effect on setting[1] | | Initial Addition | Delayed Addition |
|---|---|---|---|---|
| Bone Morphogenic Protein | | | | |
| rhBMP2 | Retarding effect | Initial setting time | 46.7 ± 1.2 min | 16.7 ± 1.2 min |
| | | Final setting time | 70 min, only hard after 120 min | 26.0 min |
| Antibiotics | | | | |
| Vancomycin hydro- | Strong retarding effect | Initial setting time | >1 h | 12.1 ± 2.7 min |
| | | Final setting time | nd | |
| Tobramycin sulfate | Strong retarding effect | Initial setting time | >1 h | 14.7 ± 5.5 min |
| | | Final setting time | nd | 22.7 min |
| Cefazolin | Retarding effect | Initial setting time | 37 ± 0 min | 10.3 ± 0.6 min |
| | | Final setting time | 52.7 ± 1.2 min | 14.3 ± 0.6 min |
| Gentamycin sulfate | Retarding effect | Initial setting time | 31 ± 0 min | 11.3 ± 0.6 min |
| | | Final setting time | 42 ± 0 min | 16.3 ± 0.6 min |
| Cephalexin hydrate | Strong retarding effect | Initial setting time | >1 h | 9.3 ± 0.6 min |
| | | Final setting time | nd | 13 ± 0 min |

[1]If IST is 30-60 min it is considered to be a "retarding effect", if IST > 1 h it is considered as a "strong retarding effect"

The above results obtained using the method according to the invention show that this method allows the admixing of a wide range of different additives such as bioactive agents having a retarding or strong retarding effect on the hardening of calcium sulfate based compositions in which a hardening of calcium sulfate hemihydrate to calcium sulfate dihydrate is to take place and that a paste having a short initial setting time is obtained.

Example 4

Figure 4A:
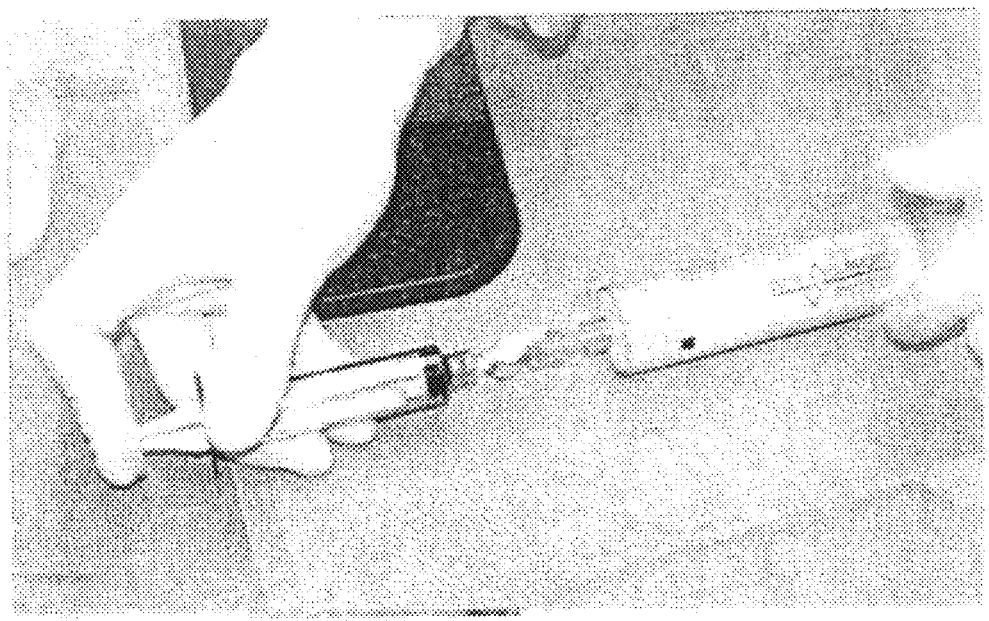
FIG. 4A-4E illustrates the manufacture of antibiotic beads impregnated with Vancomycin
Figure 4B:
Figure 4C:
Figure 4D:
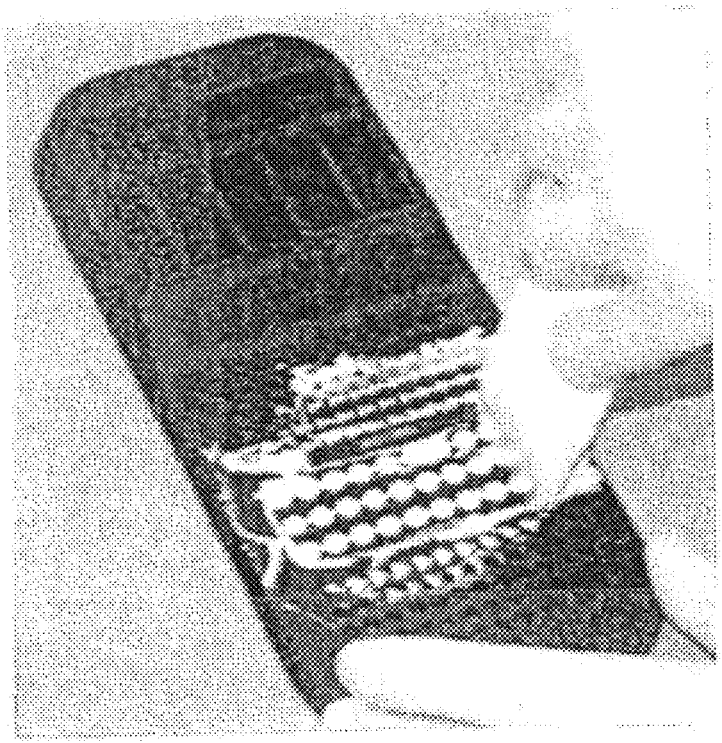
Figure 4E:
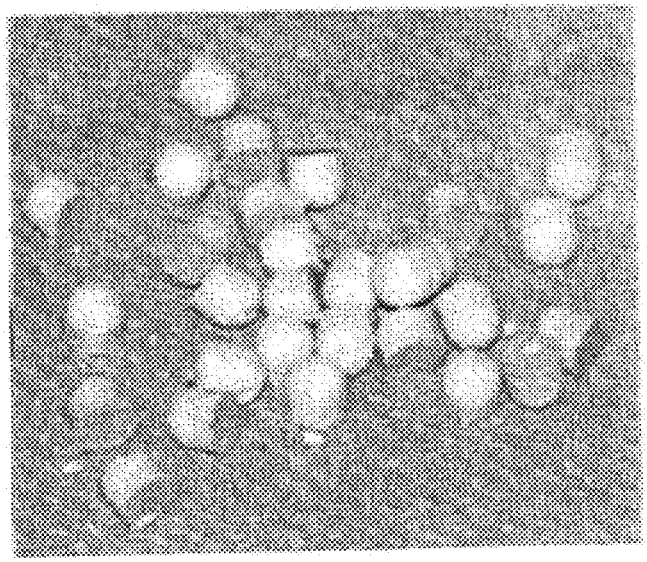

Manufacture of Antibiotic Beads Based on of Cerament™ Bone Void Filler Impregnated with Vancomycin A 10 ml Cerament™ Bone Void Filler kit was mixed with 2 grams of vancomycin utilizing the following 1-2-3-4 technique. First, the iohexyl solution was mixed with the Cerament™ Bone Void Filler with rotation of the wrist for two minutes. (FIG. 4A) At two minutes the Cerament™ Bone Void Filler was placed in a sterile bowl. (FIG. 4B) At three minutes, two grams of Vancomycin was added and mixed with a wide spatula in a rolling fashion. (FIG. 4C) By four minutes the placement of the mixture in the bead mold was completed. (FIG. 4D) At 15-20 minutes the antibiotic beads were removed from the mold and were ready for implantation. (FIG. 4E).

Example 5

Use of Antibiotic Beads Based on of Cerament™ Bone Void Filler Impregnated with Vancomycin for the Treatment of Osteomyelitis In a clinical test a 42-year-old, non-smoking diabetic male presented with chronic foot ulcers and underlying 4th metatarsal osteomyelitis and 4th/5th toe gangrene was treated. The MRSA osteomyelitis involved the fourth metatarsal and forth toe proximal phalanx. The osteomyelitis was unresponsive to both to oral and intravenous antibiotics. The gangrene had started the day before surgery. The patient's past medical history was significant for poorly controlled type 2 diabetes, hypertension, coronary artery disease with history of myocardial infarction and chronic renal insufficiency. The patient had a previous partial fifth metatarsal resection one year ago for osteomyelitis with no fourth toe, fifth toe, or fourth metatarsal involvement at that time. Lower extremity arterial non-invasive vascular studies demonstrated no significant stenotic disease. Surgical intervention was planned.

Surgical management included ulcer debridement, amputation of the 4/5 th toes, and partial resection of the forth metatarsal. The Cerament™ Bone Void Filler beads were place in apposition to the remaining fourth metatarsal. Typical closure followed. The patient progressed very well. Bone cultures demonstrated MRSA. No systemic antibiotics were given after bone resection, Bactrim DS was given orally for two weeks after the partial bone resection. The Cerament™ Bone Void Filler—vancomycin impregnated beads started to show signs of reabsorbing at fourteen days after surgery and were completely resorbed at four weeks. The diabetic ulcers were healed at eleven weeks after surgery and there were no formed beads remaining. There was HA remaining that elicited no foreign body or immune host response.

This patient had no recurrence of the osteomyelitis at six months post-op.

DISCUSSION

Cerament™ Bone Void Filler calcium sulfate and hydroxyl apatite antibiotic beads can be an effective, safe, and easy therapy in conjunction with surgical debridement for the management of osteomyelitis. A diabetic foot with MRSA osteomyelitis with successful management with surgical debridement and vancomycin Cerament™ antibiotic beads was treated. There was no local adverse reaction to the antibiotic beads and there was no osteomyelitis reoccurrence. An advantage of the Cerament™ Bone Void Filler calcium sulfate and hydroxyl apatite antibiotic beads is that because they are biodegradable, a subsequent second surgery to remove the beads is not necessary.

SUMMARY LISTING OF REFERENCES

S. Gitelis and G. T. Brebach, Journal of Orthopaedic Surgery 2002 10(1): 53-60
N. B. Sing, B. M. (2007), Progress in Crystal Growth and Characterization of Materials 53, pp 57-77
WO 2004/078223 (BONE SUPPORT AB)
K. C. Richelsoph, D. D. Webb and W. O. Haggard (2007) CLINICAL ORTHOPAEDICS AND RELATED RESEARCH, Number 461, pp 68-73
WO 01/76649 (BONE SUPPORT AB)
WO 03/053488 (BONE SUPPORT)
WO 2005/122971 (BONE SUPPORT)
WO 02/05861 (BONE SUPPORT)
U.S. Pat. No. 6,251,139 (LIN CHI-I ET AL)
WO 2005/099783 (CORIPHARM MEDIZINPRODUKTE GMBH)
WO 01/34216 (CORIPHARM MEDIZINPRODUKTE GMBH)
Jeffrey C. Karr: Management of a Diabetic Patient Presenting with Fore-foot Osteo-myelitis—The use of Cerament™ Bone Void Filler Impregnated with Vancomycin—An Off Label Use; The Journal of Diabetic Foot Complications, Volume 1, Issue 4, No. 3

The invention claimed is:

1. A method for the preparation of an injectable ready-to-use bone cement paste composition comprising
   a) preparing a mixture consisting of calcium sulfate hemihydrate, a powdered calcium phosphate component, and calcium sulfate dihydrate to form a bone cement powder,
   b) mixing the bone cement powder from step a) with water, saline, or an iohexol solution for a period of time,
   c) allowing the mixture from step b) to sit for a period of time and
   d) admixing a bioactive agent to the mixture from step c) by means of a short-duration mixing using a minimum of energy, wherein the bioactive agent has a retarding effect on the hardening of the bone cement paste, and
   wherein the injectable ready-to-use bone cement paste composition from step d) has an initial setting time of not less than 5 minutes, and
   wherein the calcium phosphate component is hydroxyl apatite in an amount ranging from 30 to 50 wt % of the dry powder.

2. The method of claim 1, wherein the calcium phosphate component is hydroxyl apatite or tricalcium phosphate.

3. The method of claim 1, wherein the mixture is left for at least 2 minutes in step c).

4. The method according to claim 1, wherein the bioactive agent is an antibiotic agent.

5. An injectable paste composition comprising a particulate calcium sulfate hemihydrate, an aqueous liquid, and a bioactive agent, said agent having a retarding effect on the hardening of the inorganic bone mineral substitute composition when admixed together with an aqueous liquid, prepared by
   a) preparing a mixture consisting of calcium sulfate hemihydrate, a powdered calcium phosphate component, and calcium sulfate dihydrate, wherein the calcium phosphate component is hydroxyl apatite in an amount ranging from 30 to 50 wt % of the dry powder to form a bone cement powder, b) mixing the bone cement powder from step a) with water, saline, or an iohexol solution for a period of time, c) allowing the mixture from step b) to sit for a period of time, and d) admixing the bioactive agent with the mixture from step c) by means of a short-duration mixing using a minimum of energy, wherein the injectable ready-to-use bone cement paste is capable of being used as a medicament for prophylactic or therapeutic treatment of a disorder related to supportive tissues in a human or non-human animal subject, which method comprises local administration to said subject of said composition comprising a prophylactic or therapeutic amount of said at least one bioactive agent, which is released from said composition, optionally while systemically and/or concomitantly administrating a pro-phylactic or therapeutic amount of at least one bioactive agent, wherein the composition from step d) has an initial setting time of not less than 5 minutes.

6. The paste according to claim 5, wherein the bioactive agent is an antibiotic agent.

7. The paste according to claim 5, wherein said paste is capable of being used as antibiotic beads for treatment of osteomyelitis.

8. The method of claim 1, wherein the mixing occurs for a period of time ranging from 10 seconds to 5 minutes.

9. The method of claim 1, wherein the mixing occurs for a period of time ranging from 20 seconds to 2 minutes.

10. The method of claim 1, wherein the mixing occurs for a period of about 30 seconds.

11. The method of claim 1, wherein the time in step c) is at least 15 seconds.

12. The method of claim 1, wherein the time in step c) is at least 1 minute.

13. The method of claim 1, wherein the initial setting time ranges from 5 minutes to 20 minutes.

14. A method for the preparation of injectable ready-to-use bone cement paste compositions comprising a) preparing a mixture consisting of 59.6 wt % calcium sulfate hemihydrate, 0.4 wt % calcium sulfate dihydrate, and 40 wt % hydroxylapatite to form a bone cement powder, b) mixing the bone cement powder from step a) with water, saline, or an iohexol solution for a period of time, c) allowing the mixture from step b) to sit for a period of time, and d) admixing a bioactive agent to the mixture from step c) by means of a short-duration mixing using a minimum of energy, wherein the bioactive agent has a retarding effect on the hardening of the bone cement paste, and wherein the injectable ready-to-use bone cement paste composition from step d) has an initial setting time of not less than 5 minutes.

15. The method of claim 14, wherein the bone cement powder of step a) is mixed with an iohexol solution.

16. The method of claim 1, wherein the bioactive agent is selected from an antioxidant, a vitamin, a hormone, an antibiotic, a cytostatic, a bisphosphonate, a growth factor, a bone marrow aspirate, or demineralised bone.

* * * * *

UNITED STATES PATENT AND TRADEMARK OFFICE
CERTIFICATE OF CORRECTION

PATENT NO. : 9,180,137 B2  
APPLICATION NO. : 13/022771  
DATED : November 10, 2015  
INVENTOR(S) : Veronica Sandell et al.

Page 1 of 1

It is certified that error appears in the above-identified patent and that said Letters Patent is hereby corrected as shown below:

ON THE TITLE PAGE

In the Abstract, item 57, line 19, there should be a new paragraph for item "d)".

IN THE CLAIMS

Claim 2, col. 18, lines 53-54, cancel claim 2 and renumber each claim and update the claim dependencies starting from claim 3.

Signed and Sealed this  
Eighth Day of March, 2016

Michelle K. Lee  
*Director of the United States Patent and Trademark Office*